United States Patent
Tsuyuki et al.

(10) Patent No.: US 10,806,419 B2
(45) Date of Patent: Oct. 20, 2020

(54) X-RAY CT APPARATUS, X-RAY CT SYSTEM, AND INJECTOR

(71) Applicant: Toshiba Medical Systems Corporation, Otawara-shi (JP)

(72) Inventors: Masaharu Tsuyuki, Nasushiobara (JP); Tatsuo Maeda, Nasushiobara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 698 days.

(21) Appl. No.: 14/992,550

(22) Filed: Jan. 11, 2016

(65) Prior Publication Data

US 2016/0113609 A1 Apr. 28, 2016

Related U.S. Application Data

(63) Continuation of application No. PCT/JP2014/068628, filed on Jul. 11, 2014.

(30) Foreign Application Priority Data

Jul. 11, 2013 (JP) .................................. 2013-145283

(51) Int. Cl.
*A61B 6/00* (2006.01)
*A61B 6/03* (2006.01)

(52) U.S. Cl.
CPC .............. *A61B 6/481* (2013.01); *A61B 6/032* (2013.01); *A61B 6/4241* (2013.01); *A61B 6/482* (2013.01);
(Continued)

(58) Field of Classification Search
None
See application file for complete search history.

(56) References Cited

U.S. PATENT DOCUMENTS 9,055,919 B2 * 6/2015 Proksa ................. A61B 5/4869
2004/0101089 A1 5/2004 Karau et al.
(Continued)

FOREIGN PATENT DOCUMENTS

JP 2004-174260 6/2004
JP 2005-312937 11/2005
(Continued)

OTHER PUBLICATIONS

International Search Report dated Oct. 7, 2014 in PCT/JP2014/068628 filed Jul. 11, 2014.
(Continued)

*Primary Examiner* — Katherine L Fernandez
*Assistant Examiner* — Yi-Shan Yang
(74) *Attorney, Agent, or Firm* — Oblon, McClelland, Maier & Neustadt, L.L.P.

(57) ABSTRACT

According to one embodiment, an X-ray CT apparatus includes a calculator, a transmitter, a data acquisition unit, and a processor. The calculator calculates a difference between imaging time phases of a first contrast agent and a second contrast agent. The transmitter sends information on the difference between the imaging time phases to an injector. The injector injects the first contrast agent and the second contrast agent into the subject at different timings based on the information. The data acquisition unit scans a subject with X-rays at a predetermined imaging timing to acquire detection data corresponding to different X-ray energies. The processor analyzes the detection data acquired at the predetermined imaging timing to generate a plurality of images corresponding to the imaging time phases.

19 Claims, 6 Drawing Sheets

(52) U.S. Cl.
CPC ............ *A61B 6/486* (2013.01); *A61B 6/5205* (2013.01); *A61B 6/542* (2013.01)

(56) References Cited

U.S. PATENT DOCUMENTS

| | | | |
|---|---|---|---|
| 2005/0018808 A1 | 1/2005 | Piacsek et al. | |
| 2006/0004279 A1 | 1/2006 | Ikeda et al. | |
| 2009/0262997 A1 | 10/2009 | Zou et al. | |
| 2010/0113887 A1* | 5/2010 | Kalafut | A61M 5/007 600/300 |
| 2011/0097273 A1 | 4/2011 | Proksa | |

FOREIGN PATENT DOCUMENTS

| | | |
|---|---|---|
| JP | 2007-105242 | 4/2007 |
| JP | 2009-261519 | 11/2009 |
| JP | 2009-261942 | 11/2009 |
| JP | 2011-528248 | 11/2011 |
| JP | 2012-223227 | 11/2012 |

OTHER PUBLICATIONS

Thorsten R. C. Johnson, et al., "Material differentiation by dual energy CT: initial experience", Eur Radiol, (17), 2007, 8 pgs.

* cited by examiner

X-RAY CT APPARATUS, X-RAY CT SYSTEM, AND INJECTOR

CROSS-REFERENCE TO RELATED APPLICATION

This application is based upon and claims the benefit of priority from Japanese Patent Application No. 2013-145283, filed Nov. 7, 2013; the entire contents of which are incorporated herein by reference.

FIELD

Embodiments described herein relate generally to an X-ray CT apparatus, an X-ray system, and an injector.

BACKGROUND

An X-ray computed tomography (CT) apparatus scans a subject with X-rays and processes acquired data by a computer, thereby imaging the inside of the subject.

Specifically, the X-ray CT apparatus exposes the subject to X-rays emitted from an X-ray tube, and detects X-rays having transmitted through the subject by an X-ray detector. Further, the X-ray CT apparatus rotates the X-ray tube and the X-ray detector to acquire detection data in different directions, and reconstructs a CT image based on the detection data.

In one method of imaging by the X-ray CT apparatus, time-series changes in the subject are measured using a contrast agent. This method involves, for example, dynamic CT examination by dynamic scanning. The "dynamic scanning" is a method of dynamic observation by continuously scanning one or more cross sections of a target site of the subject. The "dynamic CT examination" is an examination method, in which a dynamic scan is performed by using a contrast agent to analyze the time-density curve of the target site.

As to the contrast agent, the time at which the imaging effect (CT value) is the maximum varies depending on sites of the subject (e.g., artery, liver, etc.). Therefore, to obtain information at different imaging time phases by a dynamic CT examination, imaging has to be performed a plurality of times.

DETAILED DESCRIPTION

Figure 1:
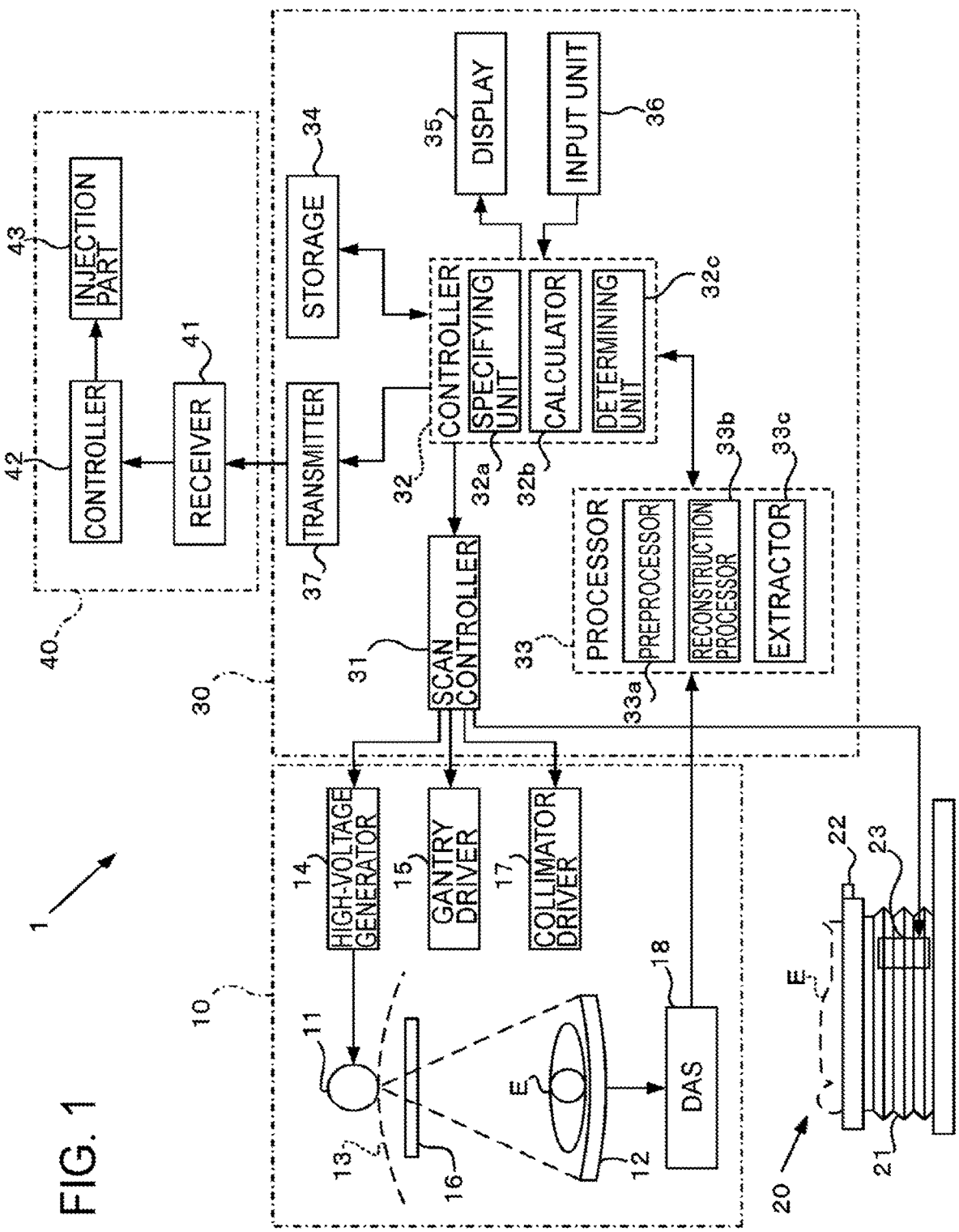
FIG. 1 is a block diagram of an X-ray CT system according to an embodiment.

In general, according to one embodiment, an X-ray CT apparatus includes a calculator, a transmitter, a data acquisition unit, and a processor. The calculator calculates a difference between imaging time phases of a first contrast agent and a second contrast agent. The transmitter sends information on the difference between the imaging time phases to an injector. The injector injects the first contrast agent and the second contrast agent into the subject at different timings based on the information. The data acquisition unit scans a subject with X-rays at a predetermined imaging timing to acquire detection data corresponding to different X-ray energies. The processor analyzes the detection data acquired at the predetermined imaging timing to generate a plurality of images corresponding to the imaging time phases.

Referring now to the drawings, a description is given of an X-ray CT apparatus, an X-ray CT system including the X-ray CT apparatus, and an injector according to embodiments. The X-ray CT apparatus and the X-ray CT system of the embodiments can be used for, for example, perfusion imaging of the hemodynamics (blood flow: flow velocity, flow rate, etc.) of a subject.

First Embodiment

As illustrated in FIG. 1, an X-ray CT system 1 of a first embodiment includes a gantry 10, a bed 20, a console 30, and an injector 40. Incidentally, the gantry 10, the bed 20 and the console 30 are an example of the X-ray CT apparatus of this embodiment.

In this embodiment, the X-ray CT system 1 uses, as an imaging method, dual-energy scanning for capturing an image by scanning a subject with a plurality of different types of tube voltages. The imaging with dual-energy scanning roughly includes at least three methods. The first method involves "slow-kV switching (dual rotation method)", in which after imaging performed with one X-ray tube at a first tube voltage, imaging is performed at a second tube voltage different from the first tube voltage. The second method involves "fast-kV switching (high-speed switching method)", in which imaging is performed by switching the tube voltage of the X-ray tube at high speed for each view during rotation (during scan). In this case, a data acquisition device acquires data in synchronization with the switching of the tube voltage to acquire data for different tube voltages in one scan. The third method involves "dual source (dual tube method)", in which not one but two X-ray tubes are used to perform imaging at different tube voltages. The fourth method involves "multi system" using an X-ray detector of a multi-layer structure. For example, when an X-ray detector of a two-layer structure (a shallow layer detector and a deep layer detector) is used, the shallow layer detector detects low-energy X-rays, while the deep layer detector detects high-energy X-rays having passed though the shallow layer detector. This embodiment is applicable to any of the above methods. In this embodiment, the second method is described.

Further, in this embodiment, an example is described in which two different types of contrast agents (first contrast agent, second contrast agent) are used. Examples of the different contrast agents include iodine-based contrast agent and gadolinium-based contrast agent.

[The Gantry]

The gantry 10 irradiates a subject E with X-rays, and acquires detection data of X-rays that have transmitted through the subject E. The gantry 10 includes an X-ray generator 11, an X-ray detector 12, a rotary body 13, a high-voltage generator 14, a gantry driver 15, an X-ray collimator 16, a collimator driver 17, and a data acquisition system (DAS) 18.

The X-ray generator 11 includes an X-ray tube (not illustrated) for generating X-rays. The subject E is exposed to the X-rays generated. In this embodiment, the X-ray generator generates a plurality of X-rays of various energies alternately for each view. The energy of X-rays can be varied by switching the tube voltage applied to the X-ray tube.

The X-ray detector 12 includes a plurality of X-ray detector elements (not illustrated), and detects X-rays having transmitted through the subject E, thereby outputting the detection data as a current signal. The X-ray detector 12 detects X-rays of different energies. For example, after detecting transmission data of a high-energy X-ray, the X-ray detector 12 detects transmission data of a low-energy X-ray. By repeating this, the X-ray detector 12 detects transmission data corresponding to the different energies.

The rotary body 13 supports the X-ray generator 11 and the X-ray detector 12 so that they face each other across the subject E. In the gantry 10, the rotary body 13 is arranged to rotate in a circular orbit centering on the subject E.

The high-voltage generator 14 applies a high voltage (tube voltage) to the X-ray generator 11. The X-ray generator generates X-rays based on the high voltage. The gantry driver 15 rotates the rotary body 13.

The X-ray collimator 16 forms the X-rays generated by the X-ray generator 11 into a fan-shaped beam or a cone-shaped beam. The collimator driver 17 drives the X-ray collimator 16 such that the X-rays generated by the X-ray generator 11 are formed into a predetermined shape.

The DAS 18 acquires data in synchronization with the switching of the tube voltage in dual-energy scanning. The DAS 18 amplifies signals of transmission data (X-ray detection data) detected by each detector element of the X-ray detector 12 to convert them to digital signals. The DAS 18 outputs the detection data converted into the digital signals to the console 30. Thus, the DAS 18 outputs high-energy and low-energy (hereinafter sometimes referred to as "dual-energy") detection data corresponding to the rotation angle of the rotary body 13 to the console 30.

[Bed]

The bed 20 is a device for placing the subject E thereon. The bed 20 includes a base 21, a top plate 22, and a bed driver 23.

The base 21 movably holds the top plate 22. The top plate 22 is a plate member where the subject E is placed. The bed driver 23 controls the base 21 to move the top plate 22 in an arbitrary direction.

[Console]

The console 30 is used for providing input to the X-ray CT apparatus. In addition, the console 30 reconstructs a CT image representing the internal structure of the subject E based on the detection data acquired by the gantry 10. The console 30 includes a scan controller 31, a controller 32, a processor 33, a storage 34, a display 35, an input unit 36, and a transmitter 37.

The scan controller 31 controls the high-voltage generator 14, the gantry driver 15, the collimator driver 17 and the bed driver 23 to operate the gantry 10 and the bed 20.

By controlling the operation of the gantry 10, the bed 20 and the console 30, the controller 32 performs the overall control of the X-ray CT apparatus. For example, the controller 32 controls the scan controller 31 to perform a pre-scan and a main scan, and thereby the gantry 10 acquires detection data. Besides, the controller 32 controls the processor 33 to perform various types of data processing or the like based on the detection data. In addition, the controller 32 displays a CT image stored in the storage 34 on the display 35.

The processor 33 performs various types of processing on the detection data detected by the gantry 10. Specifically, the processor 33 includes a preprocessor 33a, a reconstruction processor 33b, and an extractor 33c to perform the various types of processing. Incidentally, the extractor 33c is described after the description of the storage 34, the display 35, the input unit 36, the transmitter 37, and the injector 40.

<Preprocessing, Scattered Radiation Correction>

The preprocessor 33a performs logarithmic transformation and correction such as offset correction, sensitivity correction, beam hardening correction, and the like (preprocessing: processing performed before image reconstruction) on the detection data (raw data) of dual-energy fed from the DAS 18. The preprocessor 33a generates projection data by the preprocessing, and stores the data in a storage device such as the storage 34. The processor 33 removes scattered radiation from the projection data. For example, the processor 33 corrects scattered radiation by subtracting scattered radiation estimated based on the value of the target projection data to be corrected in scattered radiation or projection data adjacent thereto from the target projection data. The projection data thus corrected is, for example, stored in the storage 34.

<Isolate Reference Substance>

The processor 33 retrieves projection data of dual-energy stored in the storage 34 as pre-reconstruction data. The processor 33 may retrieve raw data instead of the projection data as the pre-reconstruction data. The processor 33 isolates (discriminate) a predetermined number of reference substances (the first contrast agent, the second contrast agent, etc.) present in the imaging target range by using the projection data of dual-energy. Described below is an example in which the processor 33 isolates two reference substances, and generates two pieces of projection data each corresponding to one of the two reference substances thus isolated. Note that the number of the projection data is not limited to two, and it may be any number greater than 1. The processor 33 feeds the reconstruction processor 33b with the two pieces of projection data corresponding to the two reference substances.

<Specify Reference Substance>

The reconstruction processor 33b reconstructs a reference substance image (reference substance enhanced image) as image data with respect to each reference substance (contrast agent) based on the two pieces of projection data each corresponding to one of the two reference substances. For example, the reconstruction processor 33b generates a reference substance image of the first contrast agent based on the projection data corresponding to the first contrast agent, and then generates a reference substance image of the second contrast agent based on the projection data corresponding to the second contrast agent. Herein, "corresponds to the contrast agent" indicates, for example, that it has been detected by scanning with X-ray energy corresponding to the K-absorption edge or the linear attenuation coefficient specific to the contrast agent. The reconstruction processor 33b sends two reference substance images thus generated, each corresponding to one of the two reference substances, to the controller 32.

The controller 32 determines (specifies) each substance (the first contrast agent, the second contrast agent, etc.) present in the imaging target range based on the two reference substance images corresponding to the two reference substances. Further, the controller 32 obtains the CT value of each substance thus determined. The controller 32 uses the first contrast agent, the second contrast agent, or the like present in the imaging target range and the CT values thereof to specify the imaging time phase described below.

Incidentally, there are roughly two methods to specify a substance with dual-energy data: image-based method for specifying a substance based on an image generated from dual-energy projection data (Japanese Unexamined Patent Application Publication No. 2009-261942), and raw-data-based method, in which two reference substances are isolated from dual-energy projection data, and images are created based on the respective reference substances to specify a substance from the images (Johnson T R et al., "Substance differentiation by dual-energy CT: initial experience", Eur Radiol (2007), 17, 1510-1517). The both can be employed in this embodiment, and other methods may also be used as long as a substance can be specified.

<Specify Imaging Time Phase>

Figure 2:
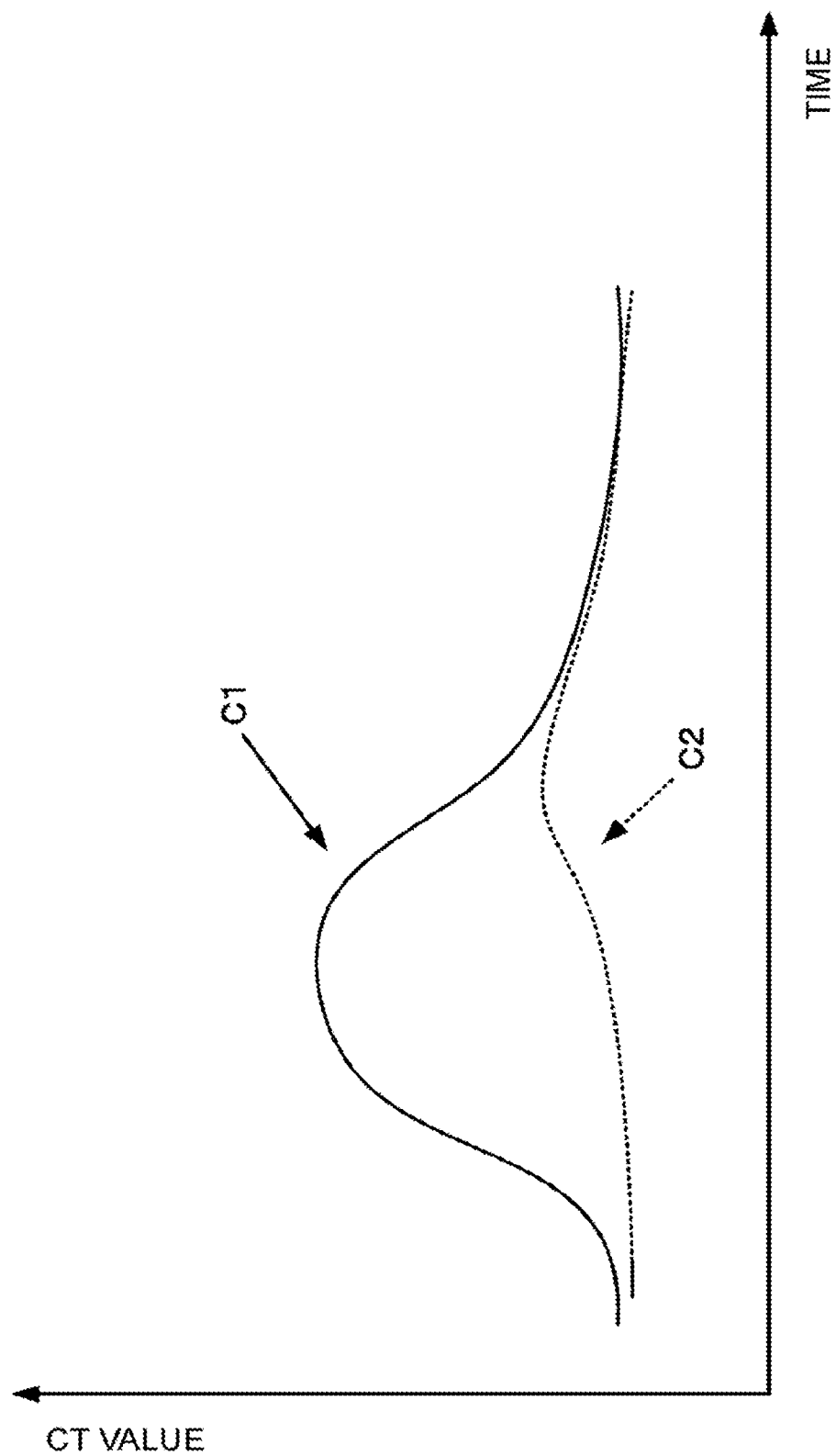
FIG. 2 is a graph for explaining the X-ray CT system of the embodiment.
Figure 3:
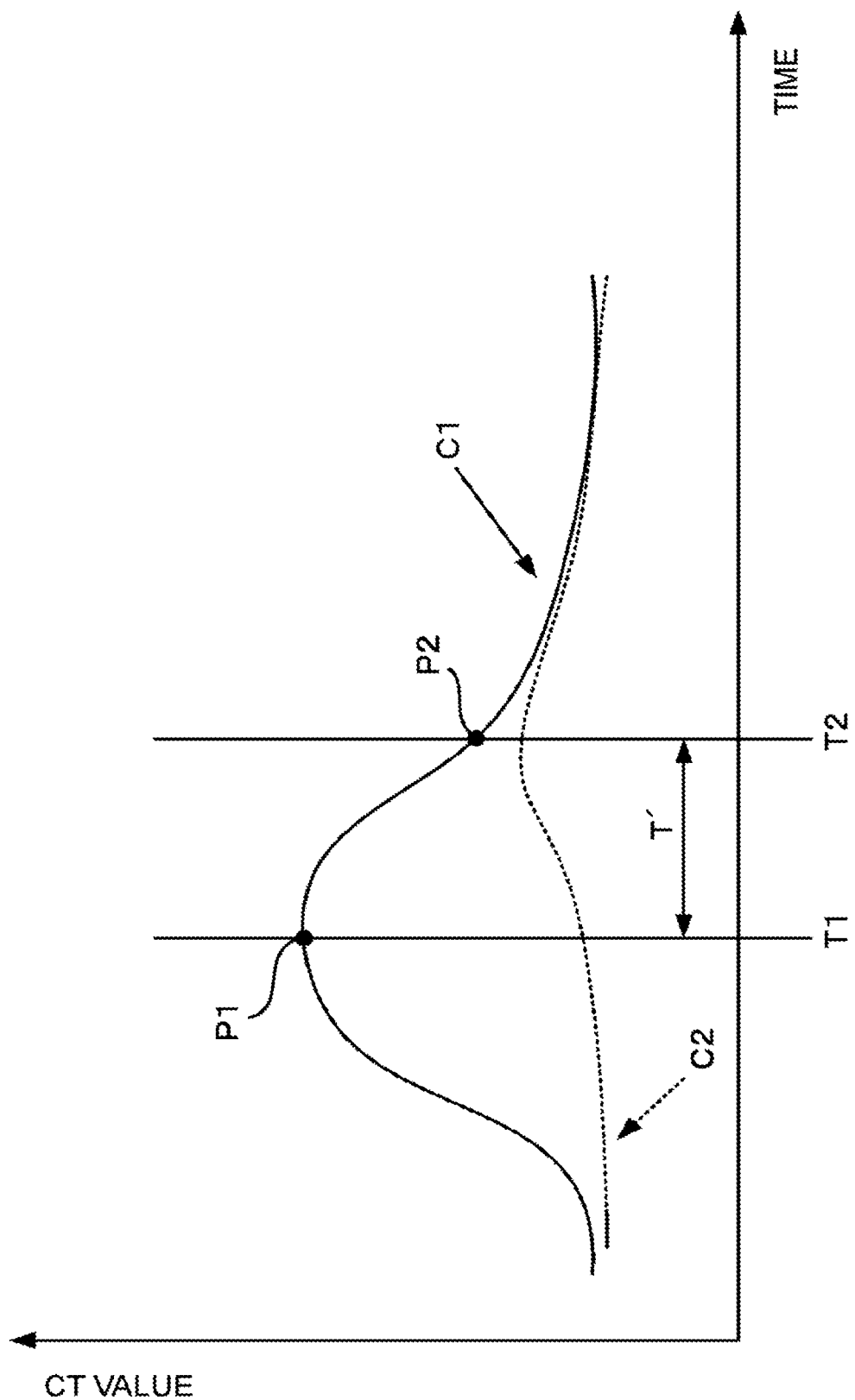
FIG. 3 is a graph for explaining the X-ray CT system of the embodiment.

The controller 32 of this embodiment also functions as a specifying unit 32a, a calculator 32b, and a determining unit 32c. In the following, a description is given of the operation of the controller 32 to specify an imaging time phase with reference to FIGS. 2 to 4. FIG. 2 illustrates an example of curves (C1, C2) indicating the time-series changes of the CT values of individual sites where the contrast agents pass through in the subject E. FIG. 3 illustrates points P1 and P2 on first and second curves where the CT values are the maximum and imaging time phases T1 and T2 corresponding to the CT values.

The "first curve" is data indicating a time-series change of the CT value of the contrast agent in detection data of X-rays that have transmitted through a first site (e.g., an artery) of the subject E (see, for example, C1 in FIG. 2). The "second curve" is data indicating the imaging time phase of the CT value of the contrast agent in detection data of X-rays that have transmitted through a second site (e.g., liver) of the subject E different from the first site (see, for example, C2 in FIG. 2).

The specifying unit 32a specifies an imaging time phase, in which the CT value is substantially the maximum, in each of the first and second curves. Specifically, with respect to the first curve C1 and the second curve C2 as illustrated in FIG. 2, the specifying unit 32a obtains the points P1 and P2 where the CT value becomes the maximum, and specifies the imaging time phases T1 and T2 corresponding to the CT value (see FIG. 3). The points P1 and P2 each correspond to an example of the "first imaging time phase" or the "second imaging time phase".

The first curve and the second curve have different shapes depending on the state of the subject, the type of the contrast agent, injection conditions of the contrast agent (the concentration of the contrast agent, the injection rate, the injection volume, etc.). It is assumed in this embodiment that the first curves as well as the second curves of the first contrast agent and the second contrast agent have the same shape.

Besides, the "substantially maximum CT value" indicates the size of the CT value where each site (the first site and the second site, etc.) becomes recognizable in the CT image. The substantially maximum CT value may be, for example, a peak value of the curve, a value larger than a predetermined threshold value, or the like. The "imaging time phase" indicates an elapsed time from a predetermined reference time. The reference time may be, for example, the injection time of the contrast agent, a time point when the contrast agent has passed through a predetermined position in the artery, or the like. Note that the curve need not necessarily be continuous data as illustrated in FIG. 2, but may be discrete data (e.g., table data representing the relationship between the elapsed time and the CT value).

The first curve and the second curve may be obtained by, for example, test injection. In the "test injection", prior to the scanning of a certain site of the subject E, a small amount of the contrast agent is injected into the subject E, and imaging is performed for one slice (a part of the site actually to be scanned). Because of imaging of just one slice, exposure to X-rays can be reduced. For example, the controller 32 creates data (hereinafter, sometimes referred to as "curve data") on the curve representing the relationship between the elapsed time and the CT value based on the results of the test injection. The curve data is stored in the storage 34, for example. Incidentally, the curve data can be obtained without the test injection. For example, a plurality of pieces of curve data may be stored in the storage 34 in advance such that corresponding one of the curve data can be retrieved and used according to the type of the contrast agent and a site to be photographed. Details are described later in a modification.

Incidentally, the imaging time phases may be manually specified by the operator through the input unit 36 or the like. In this case, for example, the display 35 displays the first curve C1 and the second curve C2 as illustrated in FIG. 2. The operator selects any points using the input unit 36 as the points P1 and P2 where the CT value is substantially the maximum. Thereby, time phases corresponding to these points may be specified as the imaging time phases T1 and T2.

<Calculate Time Difference>

The calculator 32b calculates a time difference between the injection timing of the first contrast agent and that of the second contrast agent based on the imaging time phases specified by the specifying unit 32a. Specifically, the calculator 32b calculates the difference between the imaging time phases T1 and T2 specified by the specifying unit 32a as the time difference T' between the injection timings (see FIG. 3).

<Determine Imaging Timing>

Figure 4:
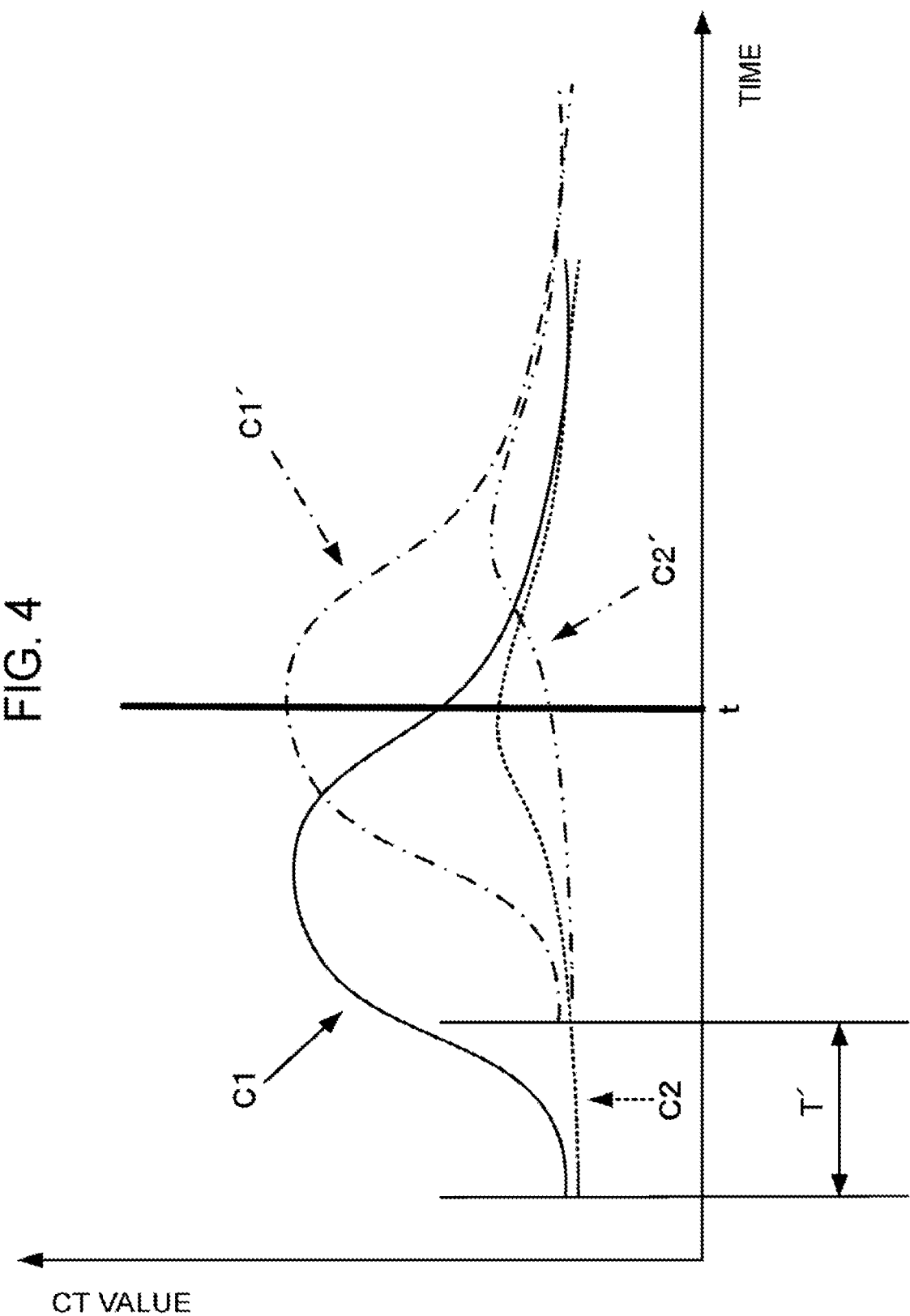
FIG. 4 is a graph for explaining the X-ray CT system of the embodiment.
Figure 5:
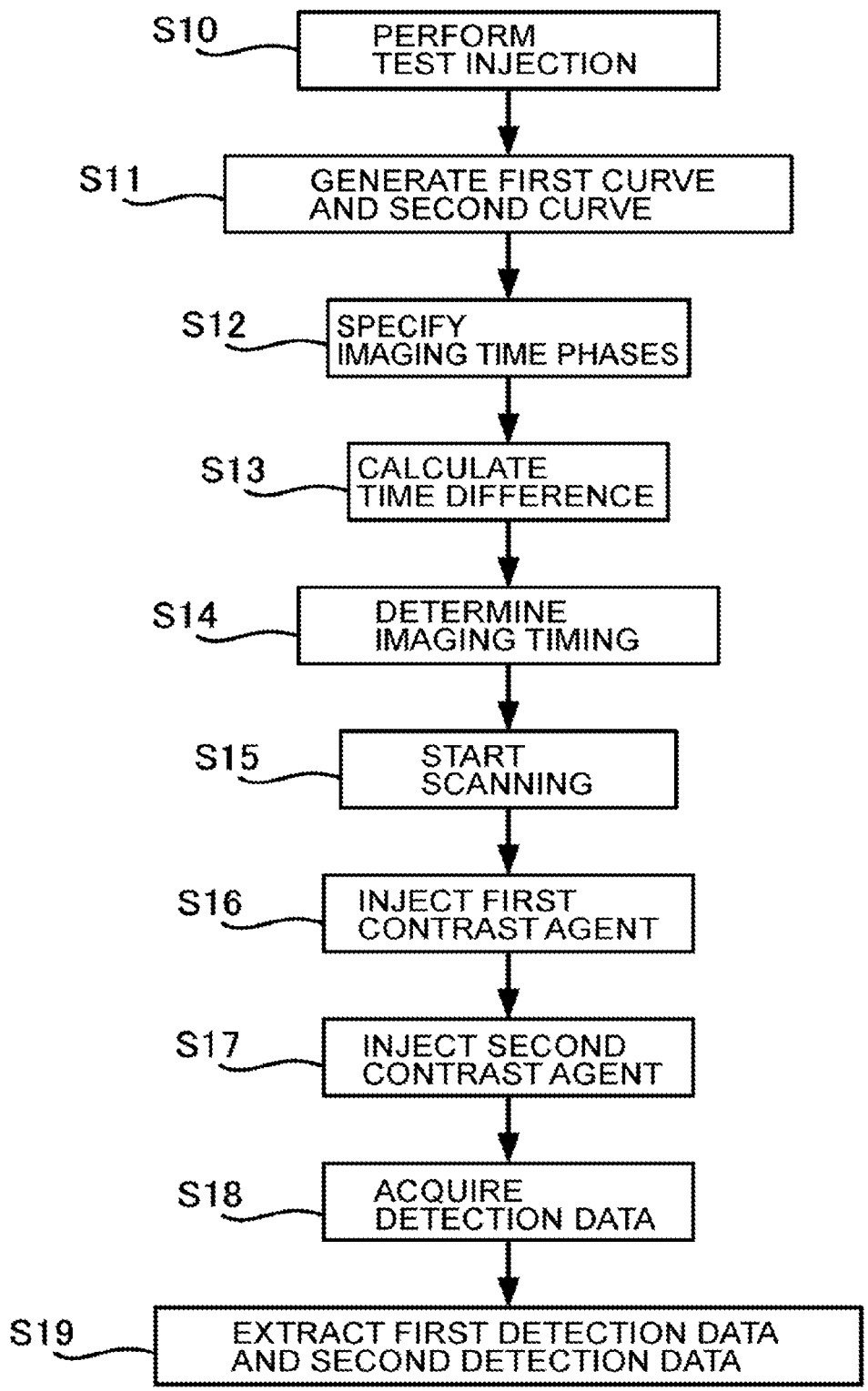
FIG. 5 is a flowchart of the operation of the X-ray CT system of the embodiment.

The determining unit 32c determines one imaging timing for the subject E based on the time difference calculated by the calculator 32b. This determination process is described with reference to FIG. 4. FIG. 4 illustrates the relationship between the first curve C1 and the second curve C2, and the first curve C1' and the second curve C2' obtained by shifting them by the time difference T'.

For example, as illustrated in FIG. 4, the determining unit 32c superimposes the first curve C1 and the second curve C2 for the first contrast agent on the first curve C1' and the second curve C2' for the second contrast agent, which has been obtained by shifting the curves C1 and C2 by the time difference T' calculated by the calculator 32b. Then, the determining unit 32c determines a time point (time t) at which the time when the CT value becomes the maximum with respect to the first site coincides with the time when the CT value becomes the maximum with respect to the second site as the imaging timing. The controller 32 controls the scan controller 31 to perform a scan at this imaging timing.

Incidentally, in response to the scan control based on the imaging timing, the injector 40 (described later) is controlled as to the injection of the contrast agent. That is, the data of the time difference T' is used for controlling the injector 40 as well as controlling the imaging timing. For example, the controller 32 controls the transmitter 37 to transmit the data of the time difference T' and the data of the injection order to the injector 40. The injection order is determined based on the imaging time phases T1 and T2 calculated as above.

The extractor 33c analyzes detection data acquired at the one imaging timing determined by the determining unit 32c to extract therefrom first detection data for the first contrast agent and second detection data for the second contrast agent. Details are described later, after the description of the injector 40.

The storage 34 is formed of a semiconductor memory such as a read only memory (ROM), a random access memory (RAM), or the like. The storage 34 stores the detection data, various types of information (first curve data, second curve data, etc.), and the like.

The display 35 includes, for example, a display device such as a cathode ray tube (CRT) or a liquid crystal display (LCD). The display 35 displays a CT image output from the processor 33 or the like.

The input unit 36 is used as an input device for performing various operations on the console 30. The input unit 36 includes, for example a keyboard, a mouse, a trackball, a joystick, and the like. The input unit 36 may further include a graphical user interface (GUI) displayed on the display 35.

The transmitter 37 transmits, to the injector 40 (receiver 41), the data of the time difference T' between the injection timings of a plurality of contrast agents calculated by the calculator 32b, and the data of the injection order via a wired or wireless communication. The transmitter 37 may also transmit an operation program or the like including the injection conditions of the injector 40 (the concentration of the contrast agent, the injection rate, the injection volume, etc.) together with the data.

[Injector]

The injector 40 is used to inject a contrast agent into the subject E. The injector 40 includes a receiver 41, a controller 42, and an injection part 43.

The receiver 41 receives the data of the time difference T' between injection timings of a plurality of contrast agents transmitted from the transmitter 37 via a wired or wireless communication. The receiver 41 may also receive the operation program or the like including the injection conditions of the injector 40, such as the concentration of the contrast agent, the injection rate, the injection volume, and the like, together with the data. The operation program is used to control the injection part 43 by the controller 42. The operation program may be stored in advance in a storage (not illustrated) inside the injector 40.

The controller 42 controls the injection part 43 to inject each of the contrast agents into the subject E based on the data of the time difference T', the data of the injection order, and the operation program received by the receiver 41. If the two types of the contrast agents are each injected into the subject E, the operation program includes, for example, injection conditions for each of the first contrast agent and the second contrast agent. Further, if the injector 40 is receiving the data of the time difference T', the controller 42 controls the injection part 43 based on the operation program as well as the data of the time difference T' and the data of the injection order.

The injection part 43 injects the contrast agent into the subject E under the control of the controller 42. For example, in the above case, the injection part 43 injects the first contrast agent and the second contrast agent into the subject E in the injection order based on the received data, with an interval of the time difference T'.

<Scan Based on Imaging Timing>

As described above, the controller 32 controls the scan controller 31 to carry out the scanning of the subject E at the imaging timing determined by the determining unit 32c. The control related to the injection of the contrast agent by the injector 40 is performed before the imaging timing. Also as described above, the imaging timing corresponds to a time point (time t) at which the CT value is the maximum in both the first site and the second site.

<Extract Detection Data>

Described below is a specific example of how to extract the detection data. By scanning based on the imaging timing, X-rays having transmitted through the target site (including the first site and the second site) of the subject E are detected. The detection data indicates a state where the CT value is the maximum in both the first site and the second site.

In the following, an example is described in which an iodine-based contrast agent is used as the first contrast agent for imaging the first site, and a gadolinium-based contrast agent is used as the second contrast agent for imaging the second site. The contrast agents have a characteristic relationship in the absorption rate and X-ray energy (keV). For example, in the case of a gadolinium-based contrast agent, the absorption rate is significantly different below and above 50 keV, i.e., the K-absorption edge. In the case of an iodine-based contrast agent, for example, the absorption rate is significantly different below and above 33.6 keV, i.e., the K-absorption edge.

As described above, various types of processing, such as preprocessing, scattered radiation correction, isolation of the reference substance, and the like, is performed on the detection data acquired by scanning based on the imaging timing. As a result, reference substance images are generated. Besides, the iodine-based contrast agent and the gadolinium-based contrast agent are determined (specified) as the first contrast agent and the second contrast agent, respectively. Further, the first contrast agent, the second contrast agent, or the like present in the imaging target range, and the CT values thereof are obtained.

Thus, in this embodiment, scan is performed with a plurality of X-ray energies. Therefore, it is possible to obtain CT images corresponding to different energies at one imaging timing. By analyzing the CT images of the different energies, it is possible to determine the imaging effect of the first contrast agent and the imaging effect of the second contrast agent. The imaging effect is a value corresponding to the concentration of the contrast agent, the X-ray absorption rate by the contrast agent, and the like. Described below is the operation of the extractor 33c related to this analysis.

The extractor 33c compares the X-ray absorption rates of the CT image around the K-absorption edge of the contrast agent used (in the case of a gadolinium-based contrast agent, 50 keV), thereby obtaining the imaging effect of the iodine-based contrast agent and that of the gadolinium-based contrast agent separately. If the detection data is based on the gadolinium-based contrast agent, the absorption rates are significantly different at energies below and above 50 keV. The imaging effect by the gadolinium-based contrast agent can be estimated from the difference between the absorption rates. The imaging effect by the iodine-based contrast agent can be obtained by removing the imaging effect by the gadolinium-based contrast agent from that of the iodine-based contrast agent and the gadolinium-based contrast agent mixed together.

While, in the above example, the first detection data and the second detection data are obtained from CT images corresponding to two energies, the detection data may be obtained by using CT images corresponding to three energies. In this case, a plurality of pieces of detection data can be obtained separately by comparing the X-ray absorption rates around the K-absorption edge of each contrast agent.

Further, although two types of contrast agents are used in the above example, three or more types of contrast agents may be used. In this case, detection data is obtained with respect to each of the contrast agents.

With the above configuration, it is possible to obtain the first detection data, which is an image representing the distribution of the imaging effect of the first contrast agent, and the second detection data, which is an image representing the distribution of the imaging effect of the second contrast agent. Incidentally, the first detection data and the second detection data are obtained from data detected by the X-ray detector 12 at approximately the same time; however, because of the difference between the injection timing of the first contrast agent and that of the second contrast agent, the imaging time phases are different. As being images having different imaging time phases, the first detection data and the second detection data represent perfusion information on the blood flow corresponding to their respective imaging time phases.

As a specific example, the controller 32 obtains a value based on the absorption rate corresponding to an arterial segment in the first image, The first image represents the imaging effect of iodine-based contrast agent. The controller 32 obtains a value based on the absorption rate corresponding to a tissue portion in the second image, The second image represents the imaging effect of gadolinium-based contrast agent. The controller 32 obtains a value related to blood perfusion based on the value obtained.

<Operation>

With reference to FIGS. 2 to 5, the operation of the X-ray CT system 1 of this embodiment is described below. The following description is given on the assumption that the same injection conditions are used for the first contrast agent and the second contrast agent.

First, after a contrast agent (e.g., the first contrast agent) is injected into the subject E by the injector 40, the X-ray CT apparatus (the gantry 10) irradiates the subject E with X-rays, and detects X-rays having transmitted through the subject E to acquire detection data (S10, test injection). Based on the detection data acquired in step S10, the controller 32 generates data that corresponds to the first curve C1 corresponding to the first site and data that corresponds to the second curve C2 corresponding to the second site (S11, see FIG. 2).

Next, the specifying unit 32a obtains the point P1 and P2 on the curves (the first curve C1 and the second curve C2) based on the data generated in step S11 where the CT values are the maximum, and specifies the imaging time phases T1 and T2 corresponding to the CT values (S12, see FIG. 3).

The calculator 32b calculates the time difference T' between the imaging time phases T1 and T2 specified in step S12 (S13, see FIG. 3). Then, data indicating the time difference T' thus calculated and the injection order is sent to the injector 40. The time difference T' may be any information related to the time difference between the injection timings of a plurality of types of contrast agents. For example, instead of the time difference, information on the imaging time phases T1 and T2 of the first and second contrast agents may be used.

The determining unit 32c determines a time point (time t) at which the CT value of the first curve C1 for the first contrast agent and that of the second curve C2' for the second contrast agent are the maximum based on the time difference T' calculated in step S13, and determines it as imaging timing (S14, see FIG. 4). The imaging timing is stored in the storage 34.

Thereafter, the X-ray CT system 1 starts scanning the subject E (S15). First, the injector 40 injects the first contrast agent into the subject E based on the operation program and the data indicating the injection order and the like (S16). The injector 40 injects the second contrast agent into the subject E based on the operation program and the data indicating the time difference T' and the injection order and the like (S17).

The X-ray CT system 1 irradiates the subject E with X-rays of different energies at one imaging timing determined in step S14, each at a predetermined timing (e.g., simultaneously). Then, the X-ray CT system 1 detects X-rays having transmitted through the subject E to acquire detection data (S18). The preprocessor 33a, the reconstruction processor 33b, and the controller 32 perform a variety of processing on the detection data. As a result, CT images (reference substance image, etc.) each corresponding to one of the X-ray energies can be obtained.

The extractor 33c analysis the CT images obtained in step S18 (e.g., specifies the reference substance), and extracts first detection data enhanced by the first contrast agent and second detection data enhanced by the second contrast agent (S19). After the image processor performs a variety of processing on the first detection data and the second detection data acquired in step S19, for example, the detection data are displayed on the display 35. When images based on the first and second detection data are displayed, the imaging time phases corresponding to these images may also be displayed. The imaging time phases may be obtained using information related to the time difference between the injection timings of the contrast agents sent to the injector 40 (information on the time difference T' or the imaging time phases T1 and T2 of the first and second contrast agents). The images based on the first and second detection data correspond to an example of "first image" and "second image". Further, for example, the image based on the first detection data illustrates an arterial segment. Besides, for example, the image based on the second detection data illustrates a tissue portion.

According to this embodiment, the X-ray CT apparatus includes the X-ray generator 11, the X-ray detector 12, the storage 34, the specifying unit 32a, the calculator 32b, the determining unit 32c, and the extractor 33c. The X-ray generator 11 generates X-rays. The X-ray detector 12 detects X-rays having transmitted through the subject E and outputs detection data. The storage 34 stores the first curve C1 indicating time-series changes of the CT value of the first contrast agent in the detection data of X-rays having transmitted through the first site of the subject E, and the second curve C2 indicating time-series changes of the CT value of the first contrast agent in the detection data of X-rays having transmitted through the second site different from the first site. The specifying unit 32a specifies imaging time phases (T1 and T2), in which the CT value is substantially the maximum, in the first curve C1 and the second curve C2. The calculator 32b calculates a time difference T' between the injection timing of the first contrast agent and the injection timing of the second contrast agent based on the imaging time phases specified by the specifying unit 32a. The determining unit 32c determines one imaging timing for the subject E based on the time difference T' calculated by the calculator 32b. The extractor 33c analyzes detection data acquired at the one imaging timing, and extracts first detection data enhanced by the first contrast agent and second detection data enhanced by the second contrast agent from the detection data.

In addition, according to the embodiment, the X-ray CT system 1 includes the injector 40 and an X-ray CT apparatus.

The X-ray CT apparatus includes the X-ray generator 11, the X-ray detector 12, the storage 34, the specifying unit 32a, the calculator 32b, the determining unit 32c, the extractor 33c, and the transmitter 37. The injector 40 injects a contrast agent into the subject E. The X-ray generator 11 generates X-rays. The X-ray detector 12 detects X-rays having transmitted through the subject E and outputs detection data. The storage 34 stores the first curve C1 indicating time-series changes of the CT value of the first contrast agent in the detection data of X-rays having transmitted through the first site of the subject E, and the second curve C2 indicating time-series changes of the CT value of the first contrast agent in the detection data of X-rays having transmitted through the second site different from the first site. The specifying unit 32a specifies imaging time phases (T1 and T2), in which the CT value is substantially the maximum, in the first curve C1 and the second curve C2. The calculator 32b calculates a time difference T' between the injection timing of the first contrast agent and the injection timing of the second contrast agent based on the elapsed time specified by the specifying unit 32a. The determining unit 32c determines one imaging timing for the subject E based on the time difference T' calculated by the calculator 32b. The extractor 33c analyzes detection data acquired at the one imaging timing, and extracts first detection data enhanced by the first contrast agent and second detection data enhanced by the second contrast agent from the detection data. The transmitter 37 transmits the time difference T' calculated by the calculator 32b to the injector 40. Then, the injector 40 injects the first contrast agent and the second contrast agent into the subject E based on the time difference T'. The X-ray CT apparatus performs imaging at the one imaging timing, analyzes detection data thus acquired, and extracts the first detection data and the second detection data therefrom.

In this manner, by extracting a plurality of pieces of detection data acquired at one imaging timing, information on different imaging time phases can be obtained by one imaging. Therefore, it is possible to reduce the positional displacement between CT images and the radiation exposure. Incidentally, the positional displacement between CT images may be caused, for example, when images of different time phases are captured by dynamic CT scan for the artery and tissue with contraction, and position registration is performed between generated images. As an example of the tissue with contraction may be cited the lung, which expands and contracts in a long cycle.

In addition, according to this embodiment, having received data on the time difference T' and the injection order of contrast agents from the X-ray CT apparatus, the injector 40 injects the first contrast agent and the second contrast agent into the subject E based on the data. The X-ray CT apparatus performs a scan in response to the injection of the contrast agent to thereby perform imaging at one imaging timing. The X-ray CT apparatus analyzes acquired detection data, and extracts first detection data and second detection data therefrom. The data on the time difference T' and the injection order of the contrast agents. That is, the data is obtained based on the first curve C1 indicating time-series changes of the CT value of the first contrast agent in the detection data of X-rays having transmitted through the first site of the subject E, and the second curve C2 indicating time-series changes of the CT value of the second contrast agent in the detection data of X-rays having transmitted through the second site different from the first site. For example, the time difference T' is the difference between imaging time phases (T1 and T2), in which the CT value is substantially the maximum, in the first curve C1 and the second curve C2.

Modification 1

The first embodiment describes an example, in which a test injection is performed upon obtaining the time difference T'. However, the embodiment is not limited to this. For example, data as follows may be stored in advance instead of performing a test injection.

As discussed above, depending on the imaging site and the types of contrast agents, a plurality of pieces of curve data may be obtained in advance based on simulation and past data without a test injection. As a specific example, the relationship between the organ to be photographed and the cardiac output for various contrast agents is parameterized in advance, and a plurality of pieces of curve data corresponding to the parameterized data is stored in the storage 34. When the operator or the like provides the input of the types of contrast agents to be injected as well as the organ of a subject to be photographed and the cardiac output, the specifying unit 32a extracts the curve data (the first curve C1 and the second curve C2) stored in advance based on the input. Incidentally, the information of the subject may be associated with, besides the cardiac output, at least one of the body weight, the body mass index (BMI), and the type of the organ. Further, the information of the contrast agents may be associated with injection conditions (the concentration of the contrast agent, the injection rate, the injection volume, etc.), and the relationship between the injection conditions and the various information of the subject. For example, if all of these pieces of information are used, the curve data to be extracted takes into account all of the types of contrast agents, the injection conditions, the cardiac output of the subject, the body weight, the BMI, and the type of the organ. However, it is assumed in this modification that these pieces of information are selectively used for the curve data acquired in advance. In addition, instead of the curve data, the imaging time phases T1 and T2 of the first contrast agent and the second contrast agent may be stored in advance.

Modification 2

While, in the above embodiment, the same injection conditions are used for the first contrast agent and the second contrast agent, different injection conditions may also be used.

If the injection conditions are different, the first curve and the second curve may have different shapes. Thus, the determining unit 32c determines one imaging timing in consideration of the injection conditions (concentration, injection rate, injection volume, etc.) and the imaging time phase.

For example, when the injection rate of one of the contrast agents is changed, it causes a change in the height of each curve and the time to reach the maximum CT value (imaging time phase). Accordingly, in this case, the determining unit 32c corrects the height of the curve of the contrast agent and the time to reach the peak according to the injection rate with reference to the other contrast agent. The determining unit 32c determines one imaging timing based on the first curve and the second curve for the other contrast agent and the first curve and the second curve for the contrast agent thus corrected Modification 3

In the above embodiment, reconstituted CT images are analyzed to obtain detection data corresponding to different contrast agents; however, it is not so limited. For example, detection data (projection data) may be analyzed prior to reconstruction to obtain detection data (projection data) each corresponding to one of the contrast agents, and thereafter, the data may be reconstructed.

Second Embodiment

In the above embodiment, a description is given of the configuration of a dual-energy system, however, the imaging system is not limited to this. Any system may be employed as long as it can measure the absorption spectrum of a plurality of X-rays. For example, "photon counting" may be used. The photon counting is a method for counting the number of photons of X-rays incident on the X-ray detector. In the following, a description is given of an X-ray CT system of a second embodiment that uses the photon counting. In the second embodiment, a photon counting X-ray CT apparatus is used. The X-ray CT apparatus of the second embodiment is described mainly about the differences from that of the first embodiment.

<X-Ray Generator>

In the X-ray CT apparatus of the second embodiment, the X-ray generator 11 performs a single-energy scan.

<X-Ray Detector>

The X-ray detector 12 includes an X-ray detector sensor that is provided with a matrix of rows of detector elements. The detector elements are intended to count light beams derived from X-rays having transmitted through the subject. For example, the channel direction of the X-ray detector sensor is designed to have a curve in consideration of the spread angle of X-ray beams emitted from the X-ray tube. The overall shape of the X-ray detector sensor is determined depending on the application, and it may be a flat-plate shape.

In one example, the detector sensor of the X-ray detector 12 of the second embodiment includes detector elements each using a cadmium telluride (CdTe)-based semiconductor. That is, the detector sensor is a direct-conversion semiconductor detector that directly converts incident X-rays into light beams and counts the light beams derived from the X-rays. The following description is given by taking the semiconductor detector as an example. Note that the X-ray detector 12 of this embodiment is not limited to the semiconductor detector, and it may use any detector capable of photon counting such as, for example, an indirect conversion detector formed of a scintillator and a photomultiplier tube.

When photons are incident on the detector elements of the detector sensor, the detector elements output an electrical signal corresponding to one pulse. By discriminating individual pulses output from the detector elements, it is possible to count the number of photons (X-ray photons) derived from X-rays incident on the detector elements. Besides, through arithmetic processing based on the intensity of the individual pulses, the energy of the photons counted can be measured.

<DAS>

The DAS 18 acquires a counting result, which is a result of the counting, by using an output signal from the X-ray detector. The DAS 18 counts photons derived from X-rays having emitted from the X-ray generator 11 and transmitted through the subject E. In addition, the DAS 18 acquires a result of measuring the energy of the photons counted as a counting result. The DAS 18 sends the counting result to the console 30.

Specifically, the DAS 18 acquires the incident position (detected position) of X-ray photons counted by discriminating pulses output from the detector elements and the energy value of the X-ray photons as the counting result with respect to each phase (tube phase) of the X-ray generator 11. The DAS 18 may use, for example, the position of each detector element having output a pulse used for the counting as the incident position. Further, the DAS 18 calculates the energy value from, for example, the peak value of the pulse and a system-specific response function. Alternatively, for example, the DAS 18 calculates the energy value by integrating the intensity of the pulses.

For example, the counting result is information indicating that, in a predetermined tube phase, at a predetermined incident position (detector element), the count of photons having an energy "E1" is "N1". Similarly, the count of photons having an energy "E2" is "N2".

For another example, the counting result is information indicating that, in a predetermined tube phase, at a predetermined incident position (detector element), the count of photons having an energy "E1" per unit time is "n1". Likewise, the count of photons having an energy "E2" per unit time is "n2".

<Preprocessing, Scattered Radiation Correction>

The preprocessor 33a performs correction processes (preprocessing) such as logarithmic conversion, offset correction, sensitivity correction, and beam hardening correction to generate projection data, and stores the data in a storage device such as the storage 34. Besides, the processor 33 removes scattered radiation from the projection data.

<Isolate Reference Substance>

The projection data generated from the counting result obtained by the photon counting CT includes information on the energy of X-rays attenuated after having transmitted through the subject P. For this reason, the reconstruction processor 33b can reconstruct, for example, X-ray CT image data (corresponding to the "reference substance image" of the first embodiment) for a specific energy component or each of a plurality of energy components.

In addition, the reconstruction processor 33b can generate image data that enables the first contrast agent and the second contrast agent to be identified by using the K-absorption edge specific to each of the contrast agents.

<Specify Reference Substance>

The controller 32 determines (specifies) each substance (the first contrast agent, the second contrast agent, etc.) present in the imaging target range based on the image data generated by the reconstruction processor 33b. Incidentally, the storage means of this embodiment, such as the storage 34, stores information on the X-ray absorption spectrum of each of a plurality of substances.

Figure 6:
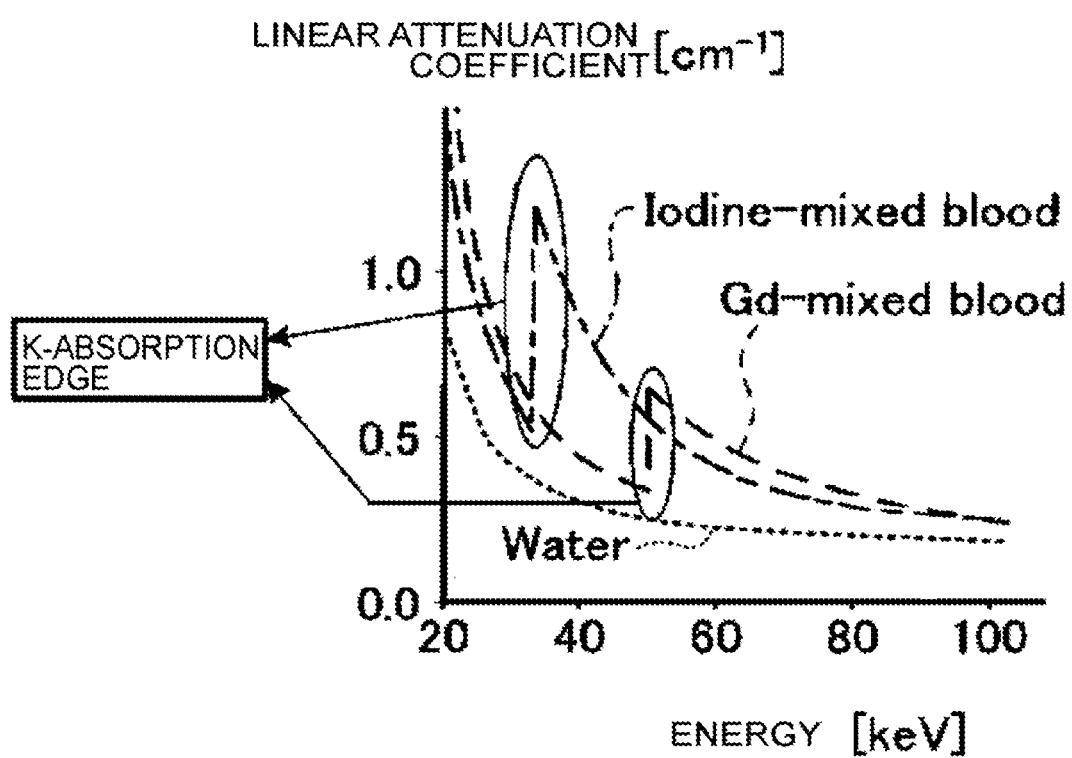
FIG. 6 is a graph for explaining a K-absorption edge of the embodiment.

In the following, the K-absorption edge is described as an example of the energy component specific to the substance with reference to FIG. 6. FIG. 6 is a graph for explaining the K-absorption edge. FIG. 6 illustrates the X-ray absorption spectra of various substances. In FIG. 6, the horizontal axis represents the energy (keV), and the vertical axis represents the linear attenuation coefficient (cm-1).

FIG. 6 illustrates the X-ray absorption spectrum of the blood mixed with an iodine-based contrast agent (Iodine-mixed blood), and the X-ray absorption spectrum of the blood mixed with a gadolinium-based contrast agent (Gd-mixed blood), together with the X-ray absorption spectrum of water (Water).

As illustrated in FIG. 6, the attenuation coefficient increases rapidly around the K-absorption edge. For example, in the case of the K-absorption edge of iodine at 33.16 keV as the substance of interest, the count of X-ray photons, which have transmitted through the tissue where an iodine-based contrast agent is present, greatly varies in an energy range of around 33.16 keV.

Accordingly, by referring to the energy range taking into account the K-absorption edge of each contrast agent for the X-ray CT image data reconstructed by the photon counting CT, a plurality of contrast agents can be discriminated. More specifically, in this embodiment, the gantry 10 continuously or intermittently scans each site through which the contrast agents pass in the subject E. Thereby, the X-ray CT image data is generated in the console 30. When each of the contrast agents flows in each site of the subject within the scan range specifically to the tissue, the X-ray attenuation coefficient increases rapidly around the K-absorption edge of the contrast agent. Incidentally, if a test injection is not performed, the imaging timing is determined based on data stored in advance as described in the above modification.

<Specify Imaging Time Phase>

The specifying unit 32a specifies the imaging time phases T1 and T2, in which the X-ray attenuation coefficient sharply increases around the K-absorption edge of each contrast agent.

<Calculate Time Difference>

The calculator 32b calculates a difference between the imaging time phases T1 and T2 specified by the specifying unit 32a as the time difference T' in the injection timing.

<Determine Imaging Timing>

The determining unit 32c determines one imaging timing for the subject E based on the time difference calculated by the calculator 32b.

The transmitter 37 transmits, to the injector 40 (the receiver 41), the data of the time difference T' between the injection timings of the contrast agents calculated by the calculator 32b, and the data of the injection order via a wired or wireless communication. The transmitter 37 may also transmit the operation program or the like including the injection conditions of the injector 40 (the concentration of the contrast agent, the injection rate, the injection volume, etc.) together with the data.

In this embodiment, a scan can be performed with a single-energy, and CT images corresponding to different energies can be obtained at one imaging timing. Besides, in the case of photon counting CT, by referring to the energy range taking into account the K-absorption edge of each contrast agent and comparing the linear attenuation coefficients, a plurality of contrast agents can be discriminated. Thus, it is possible to determine the imaging effect of the first contrast agent and that of the second contrast agent.

That is, the extractor 33c compares the linear attenuation coefficients of the CT images around the K-absorption edge of contrast agents used. Thereby, it is possible to obtain the imaging effects of different contrast agents, such as an iodine-based contrast agent and a gadolinium-based contrast agent, separately.

In the above example, the first detection data and the second detection data are obtained from CT images corresponding to two energies; however, detection data may be obtained from CT images corresponding to three energies. In this case, by comparing the X-ray absorption rates around the K-absorption edge of individual contrast agents, a plurality of pieces of detection data can be obtained separately.

While two types of contrast agents are used in the above example, three types of contrast agents may also be used. In this case, detection data is obtained with respect to each of the contrast agents.

With the above configuration, it is possible to obtain an image representing the distribution of the imaging effect of the first contrast agent as the first detection data, and an image representing the distribution of the imaging effect of the second contrast agent as the second detection data. Note that although the first detection data and the second detection data are obtained from the data detected by the X-ray detector 12 at the same time, their imaging time phases are different because of the difference between the injection timings of the first contrast agent and the second contrast agent. Since the first detection data and the second detection data are images having different imaging time phases, they represent perfusion information of the blood flow corresponding to their respective imaging time phases.

As a specific example, the controller 32 obtains a value based on a linear attenuation coefficient corresponding to an arterial segment in the first image, The first image represents the imaging effect of iodine-based contrast agent. The controller 32 obtains a value based on a linear attenuation coefficient corresponding to a tissue portion in the second image. The second image represents the imaging effect of gadolinium-based contrast agent. The controller 32 obtains a value related to blood perfusion based on the value obtained.

According to this embodiment, the X-ray CT apparatus includes the X-ray generator 11, the X-ray detector 12, the specifying unit 32a, the calculator 32b, the determining unit 32c, and the extractor 33c. The X-ray generator 11 generates X-rays. The X-ray detector 12 detects X-rays having transmitted through the subject E and outputs detection data. The specifying unit 32a specifies an imaging time phase (T1 and T2), in which the X-ray attenuation coefficient rapidly increases around the K-absorption edge of each contrast agent. The calculator 32b calculates a time difference T' between the injection timing of the first contrast agent and the injection timing of the second contrast agent based on imaging time phases specified by the specifying unit 32a. The determining unit 32c determines one imaging timing for the subject E based on the time difference T' calculated by the calculator 32b. The extractor 33c analyzes detection data acquired at the one imaging timing. By referring to the energy range taking into account the K-absorption edge of each contrast agent and comparing the linear attenuation coefficients, the different contrast agents can be discriminated. Thus, it is possible to determine the imaging effect of the first contrast agent and that of the second contrast agent.

In addition, according to the embodiment, the X-ray CT system 1 includes the injector 40 and an X-ray CT apparatus. The X-ray CT apparatus includes the X-ray generator 11, the X-ray detector 12, the storage 34, the specifying unit 32a, the calculator 32b, the determining unit 32c, the extractor 33c, and the transmitter 37. The injector 40 injects a contrast agent into the subject E. The X-ray generator 11 generates X-rays. The X-ray detector 12 detects X-rays having transmitted through the subject E and outputs detection data. The specifying unit 32a specifies an imaging time phase (T1 and T2), in which the X-ray attenuation coefficient rapidly increases around the K-absorption edge of each contrast agent. The calculator 32b calculates a time difference T' between the injection timing of the first contrast agent and the injection timing of the second contrast agent based on the elapsed time specified by the specifying unit 32a. The determining unit 32c determines one imaging timing for the subject E based on the time difference T' calculated by the calculator 32b. The extractor 33c analyzes detection data acquired at the one imaging timing. By referring to the energy range taking into account the K-absorption edge of each contrast agent and comparing the linear attenuation coefficients, the different contrast agents can be discriminated. Thus, it is possible to obtain the imaging effect of the first contrast agent and that of the second contrast agent. The transmitter 37 transmits the time difference T' calculated by the calculator 32b to the injector 40. Then, the injector 40 injects the first contrast agent and the second contrast agent into the subject E based on the time difference T' and the data of the injection order. The X-ray CT apparatus performs imaging at the one imaging timing, analyzes detection data thus acquired, and extracts the first detection data and the second detection data therefrom.

In this manner, by extracting a plurality of pieces of detection data acquired at one imaging timing, information on different imaging time phases can be obtained by one imaging. Therefore, it is possible to reduce the positional displacement between CT images and the radiation exposure. Incidentally, the positional displacement between CT images may be caused, for example, when images of different time phases are captured by dynamic CT scan for the artery and tissue with contraction, and position registration is performed between generated images.

As an example of the tissue with contraction may be cited the lung, which expands and contracts in a long cycle. Further, the photon counting CT can improve the energy resolution as compared with the first embodiment. Even in a narrow energy range, a plurality of contrast agents can be discriminated with higher accuracy. Therefore, three or more contrast agents can be used.

In addition, according to this embodiment, having received data on the time difference T' and the injection order of contrast agents from the X-ray CT apparatus, the injector 40 injects the first contrast agent and the second contrast agent into the subject E based on the data. The X-ray CT apparatus performs a scan in response to the injection of the contrast agent to thereby perform imaging at one imaging timing. The X-ray CT apparatus analyzes acquired detection data, and extracts first detection data and second detection data therefrom. The data on the time difference T' and the injection order of the contrast agents are obtained in advance.

Incidentally, the modifications 1 to 3 of the first embodiment can also be applied to the second embodiment. However, in the modification 1 of the second embodiment, what is stored in advance is not curve data, but the imaging time phases T1 and T2 of the first contrast agent and the second contrast agent.

While certain embodiments have been described, these embodiments have been presented by way of example only, and are not intended to limit the scope of the inventions. Indeed, the novel embodiments described herein may be embodied in a variety of other forms; Further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus, comprising:
    processing circuitry configured to
        calculate a difference in injection timing between a first contrast agent and a second contrast agent to be injected into a subject, wherein the difference in injection timing is calculated depending on a type of each of the first contrast agent and the second contrast agent, injection conditions of each of the first contrast agent and the second contrast agent, an organ to be scanned, and cardiac output;
        send information on the calculated difference in injection timing to an injector;
        control a scan controller to scan the subject with X-rays at an imaging timing at which an imaging effect of the first contrast agent is appearing in an artery of the organ and an imaging effect of the second contrast agent is appearing in a tissue of the organ in an imaging target range at a same time to acquire detection data corresponding to different X-ray energies, wherein the first contrast agent and the second contrast agent are injected into the subject by the injector at different injection timings based on the calculated difference in injection timing; and
        analyze the acquired detection data acquired at the imaging timing to generate a first image representing the imaging effect of the first contrast agent and a second image representing the imaging effect of the second contrast agent.

2. The X-ray CT apparatus of claim 1, wherein the processing circuitry is further configured to calculate the difference in injection timing based on X-ray detection data of the subject obtained in advance.

3. The X-ray CT apparatus of claim 1, wherein the processing circuitry is further configured to obtain a value related to blood perfusion from a value based on a linear attenuation coefficient corresponding to an arterial segment in the first image and a value based on a linear attenuation coefficient corresponding to a tissue portion in the second image.

4. The X-ray CT apparatus of claim 3, wherein an injection timing of the second contrast agent is set such that concentration of the second contrast agent is substantially maximum in the tissue portion in the second image at the imaging timing.

5. The X-ray CT apparatus of claim 1, wherein the difference in injection timing is calculated based on information that indicates time-series changes of a CT value of the first contrast agent in an arterial segment and information that indicates time-series changes of a CT value of the second contrast agent in a tissue of the subject.

6. The X-ray CT apparatus of claim 1, wherein an injection timing of the first contrast agent is set such that a concentration of the first contrast agent is substantially maximum in an arterial segment in the first image at the imaging timing.

7. The X-ray CT apparatus of claim 1, wherein the processing circuitry is further configured to send at least one of the injection conditions or an injection order of the first contrast agent and the second contrast agent to the injector together with the information on the calculated difference in injection timing.

8. An X-ray CT system, comprising:
    an injector configured to inject a contrast agent into a subject, and
    an X-ray CT apparatus configured to perform X-ray imaging of the subject, the X-ray CT apparatus including processing circuitry configured to:
        calculate a difference in injection timing between a first contrast agent and a second contrast agent to be injected into a subject, wherein the difference in injection timing is calculated depending on a type of each of the first contrast agent and the second contrast agent, injection conditions of each of the first contrast agent and the second contrast agent, an organ to be scanned, and cardiac output;

send information on the calculated difference in injection timing to the injector;

control a scan controller to scan the subject with X-rays at an imaging timing at which an imaging effect of the first contrast agent is appearing in an artery of the organ and an imaging effect of the second contrast agent is appearing in a tissue of the organ in an imaging target range at a same time to acquire detection data corresponding to different X-ray energies, wherein the first contrast agent and the second contrast agent have been injected into the subject by the injector at different injection timings based on the difference in injection timing; and analyze the acquired detection data acquired at the imaging timing to generate a first image representing the imaging effect of the first contrast agent and a second image representing the imaging effect of the second contrast agent.

9. The X-ray CT system of claim 8, wherein
the different injection timings correspond to the imaging timing, and
the imaging timing arrives after the different injection timings.

10. The X-ray CT apparatus of claim 1, wherein the processing circuitry is further configured to calculate the difference in injection timing according to a target site included in the imaging target range.

11. The X-ray CT system of claim 8, wherein the processing circuitry is further configured to calculate the difference in injection timing based on X-ray detection data of the subject obtained in advance.

12. The X-ray CT system of claim 8, wherein the difference in injection timing is calculated based on information that indicates time-series changes of a CT value of the first contrast agent in an arterial segment and information that indicates time-series changes of a CT value of the second contrast agent in a tissue of the subject.

13. The X-ray CT system of claim 8, wherein an injection timing of the first contrast agent is set such that a concentration of the first contrast agent is substantially maximum in an arterial segment in the first image at the imaging timing.

14. The X-ray CT system of claim 8, wherein the processing circuitry is further configured to send at least one of the injection conditions or an injection order of the first contrast agent and the second contrast agent to the injector together with the information on the calculated difference in injection timing.

15. A method, comprising:
calculating a difference in injection timing between a first contrast agent and a second contrast agent to be injected into a subject by an injector, the difference in injection timing depending on a type of each of the first contrast agent and the second contrast agent, injection conditions of each of the first contrast agent and the second contrast agent, an organ to be scanned, and cardiac output;

scanning, using a X-ray CT scanner, the subject with X-rays at an imaging timing at which an imaging effect of the first contrast agent is appearing in an artery of the organ and an imaging effect of the second contrast agent is appearing in a tissue of the organ in an imaging target range at a same time to acquire detection data corresponding to different X-ray energies, wherein the first contrast agent and the second contrast agent are injected into the subject by the injector at different injection timings based on the difference in injection timing; and analyzing the detection data acquired at the imaging timing to generate a first image representing the imaging effect of the first contrast agent and a second image representing the imaging effect of the second contrast agent.

16. The method of claim 15, further comprising calculating the difference in injection timing based on X-ray detection data of the subject obtained in advance.

17. The method of claim 15, wherein the difference in injection timing is calculated based on information that indicates time-series changes of a CT value of the first contrast agent in an arterial segment and information that indicates time-series changes of a CT value of the second contrast agent in a tissue of the subject.

18. The method of claim 15, wherein an injection timing of the first contrast agent is set such that a concentration of the first contrast agent is substantially maximum in an arterial segment in the first image at the imaging timing.

19. The method of claim 15, further comprising sending at least one of the injection conditions or an injection order of the first contrast agent and the second contrast agent to the injector together with the information on the calculated difference in injection timing.

* * * * *